United States Patent [19]

Linker, Sr. et al.

[11] Patent Number: 5,045,710
[45] Date of Patent: * Sep. 3, 1991

[54] COPLANARITY INSPECTION MACHINE

[75] Inventors: Frank V. Linker, Sr., Springfield; Edward T. Claffey, Aston, both of Pa.

[73] Assignee: American Tech Manufacturing, Corp., Glenolden, Pa.

[ * ] Notice: The portion of the term of this patent subsequent to Feb. 26, 2008 has been disclaimed.

[21] Appl. No.: 526,162

[22] Filed: May 21, 1990

Related U.S. Application Data

[63] Continuation-in-part of Ser. No. 427,797, Oct. 27, 1989, Pat. No. 4,996,439.

[51] Int. Cl.$^5$ .............................................. G01V 9/04
[52] U.S. Cl. ........................................ 250/561; 33/645
[58] Field of Search ............... 250/561, 230; 356/376, 356/381; 33/645

[56] References Cited

U.S. PATENT DOCUMENTS 3,278,023 10/1966 Schneider ........................... 250/230
4,739,175 4/1988 Tamura ............................... 250/561
4,814,621 3/1989 Soth et al. ........................... 250/561

Primary Examiner—David C. Nelms
Assistant Examiner—Que T. Le
Attorney, Agent, or Firm—Eugene E. Renz, Jr.

[57] ABSTRACT

Apparatus for determining coplanarity of a plurality of points, comprising linear motion unit for moving an object along an linear axis. The object has a plane generally perpendicular to the axis. A gage defines a known plane which is also perpendicular to the axis and has a plurality of points thereon corresponding to points on the object. The gage also is adapted to move along the axis by said linear motion unit. Digital signal switches having individual sensors aligned on the axis for contact with the object and the gage are provided to send a set of signals to indicate the position of the object along the axis at each of the points and to provide a reference set of signals when contacted by the corresponding points on the gage. Also included is a comparator means for comparing the signals with the reference signals for each point and the corresponding point on the gage plane to identify the deviation of each point from coplanarity.

11 Claims, 2 Drawing Sheets

COPLANARITY INSPECTION MACHINE

This invention is a continuation-in-part of parent application, Ser. No. 07/427,797, filed Oct. 27, 1989 now U.S. Pat. No. 4,996,439 and entitled COPLANARITY INSPECTION MACHINE.

FIELD OF THE INVENTION

The present invention relates to a coplanarity inspection machine and more particularly to a device for determining coplanarity of multiple lead devices such as those used in the electronics industry.

BACKGROUND OF THE INVENTION

Many objects are so fragile that contacting them at all subjects them to damaging stress. Some fragile surfaces, however, can withstand a light force and therefore can be subjected to direct measurement in which contact occurs.

This ability to contact fragile objects is of particular importance in the manufacture of semi-conductor packages which are applied to the surface of a printed circuit board. When a plurality of leads extend from a single device, it often times is necessary to determine if all of the leads are appropriately arranged for contact on the printed circuit board. Particularly when multiple leads extend in the same direction, so that the device is mounted on the surface of the printed circuit board and is suspended above the board by the leads, it is necessary that these leads all make contact with the surface of the PC board. It is particularly important to have complete contact with all of the leads since each lead is essential for the total functionality of the device.

Nevertheless, there is no conventional measurement means to determine whether or not all of the leads of a surface mounted device (SMD) are in the same plane, so that appropriate and effect contact with the surface of the printed circuit board can be achieved. Linear probes and micrometers have not been successful in achieving the degree of accuracy needed for error free manufacturing. Also, use of these inadequate methods as described above can often times cause more of the individual leads to be non-aligned and therefore causes more problems than it solves.

One device which has been suggested is shown in U.S. Pat. No. 4,774,768, in which leads contact a non conductive post to overcome a spring or bias. In this patent a non conductive spacer is used to verify that all of the leads break contact with the lead within the thickness of that spacer. However, if the spacer is too thin, false reading are made and if it is too thick, the data is meaningless. In any event, even with an approximately sized spacer, coplanarity is really not being measured.

Presently, non-contacting calibration methods are employed in which lasers are aligned to measure an absolute distance. However, these designs require very careful alignment and are extremely expensive as well. A totally automated system using a laser would be prohibitively expensive. It would be a great advantage to the art if a device could be provided which would allow contacting the various leads of a SMD prior to mounting it on a printed circuit board to determine that all of the leads are within the required degree of coplanarity. In this manner, the mounting of the SMD would be highly reliable and effective during automated assembly of the completed device.

With the foregoing in mind, it is an object of the present invention to provide a method for accurately determining the coplanarity of the individual leads in a SMD.

Another object of the present invention is to provide apparatus which is suitable for accurately measuring deviations of various points in a plane from coplanarity of that plane.

Still another object of the present invention is to provide a device which can automatically display the location of individual leads on an SMD which are outside of an acceptable limit for coplanarity.

Yet another object of the present invention is to provide a signal device for use for with SMD and other sensitive or fragile articles of manufacture.

SUMMARY OF THE INVENTION

It has now been discovered that the above and other objects of the present invention can be accomplished in the following manner. Specifically, a signal device has been discovered for operation on a path in order to generate a digital signal. The device includes a movable support means which is aligned to move a SMD along that path. Also included is a sensor generating means positioned to provide a signal when contacted by the SMD at a pre-determined location on the path.

In one embodiment of the present invention, the device described above interacts with an object and a reference object, so as to provide a signal and a reference signal for comparison there between. A plurality of such devices can be used to provide a plurality of signals, in one case generated by a reference plane and in the other case by various points on an object to be measured, so that the coplanarity of the object can be determined.

When specifically designed for determining the coplanarity of multiple lead devices, such as SMDs, the device includes a means for providing a set of signals upon intersection with individual leads of the SMD as the SMD is moved along a linear axis. A reference set of signals is also provided upon intersection upon corresponding points in a known plane which is moved along that axis, such as with a gage means. In addition, there is a means for identifying the deviation between the signal from each lead and the corresponding reference signal from the plane, to thereby identify the deviation of each lead from coplanarity.

In another embodiment, the device is provided for determining coplanarity of a multiple lead device. A linear motion means is provided for moving a multiple lead device such as an SMD along a linear axis. Particularly preferred are gull wing lead devices and "J" lead devices. A gage means is also provided, having a known plane with points thereon corresponding to the various leads on the multiple lead device. The gage means and the multiple lead device are adapted to move along the axis by the linear means. A signal means is positioned at a fixed location along that axis for providing a set of signals when contacted by each of the leads indicating the lead position on that axis and also providing a reference set of signals when contacted by corresponding points on the plane carried or defined by the gage means in order to indicate the position of those points on that axis. Finally, comparator means are provided for comparing the signal with the reference signal for each lead and the corresponding point in the plane, in order to identify the deviation of each lead from coplanarity.

In a specific embodiment of the present invention, the device for determining coplanarity of a multiple lead device includes a plurality of tines which are fixably mounted and have a movable or free end. A signal means is associated with each of the tines and is adapted to generate a signal upon contact and deflection by either a gage or by the individual lead with which it is associated. A linear motion means is provided to transport a multiple lead device along a linear axis which is generally perpendicular to the plane of the leads. A gage means defining a known plane having points thereon corresponding to the individual leads of the multiple lead device is also provided. The gage means is adapted to move along the axis using the linear motion means and intersect the tines. Comparator means are provided for comparing the reference signal when each tine is deflected upon movement of the gage means along the axis with the signal generated when each tine is deflected by a lead of the multiple lead device moved along that axis. The comparator will then identify the deviation of each lead from a coplanarity.

BRIEF DESCRIPTION OF THE DRAWINGS

These and other objects of the present invention and the various features and details of the operation and construction thereof are hereinafter more fully set forth with reference to the accompanying drawings, where.

DETAILED DESCRIPTION OF THE PREFERRED EMBODIMENT

As is noted, it would be highly desirable to measure the contacting surfaces of the leads of semi-conductor packages at the point where they will make contact with the surface of the printed circuit board. This measurement is expressed as the coplanarity of the leads. It is desirable in the eyes of many electronic equipment manufacturers to use surface mounting procedures for multi-leaded electronic packages rather through hole mounting. Surface mounting requires extreme accuracy of the coplanarity of the leads to ensure that proper solder wicking takes place.

In its simplest form the present invention employs a switch or signal generating device which recognizes the arrival of the leads from an electronic surface mounted device (SMD) and compares the arrival location with the location of a standardized or reference plane. The difference of location on the axis between the lead and corresponding point on the reference plane indicates the degree of coplanarity.

The preferred switch of the present invention comprises a thin tine made of spring material which is secured or clamped preferably at one end and is in contact with and suspended over a conductive element, forming a complete circuit. The circuit includes means to identify when contact between the tine and the conductive element is broken, so that a signal is sent indicative of the presence of an object at a certain location along the axis of inquiry. The tine is biased for contact with the conductive element.

A linear motion encoder is used to locate the position of the various objects being moved along the path for intersection with the tine. As the SMD leads move into the tines, the linear encoder records the trip point at which each tine causes a break in the circuit. Prior to this, a reference point corresponding to each individual lead is measured by moving a flat gage block which has been manufactured to have a known coplanarity.

Figure 1:
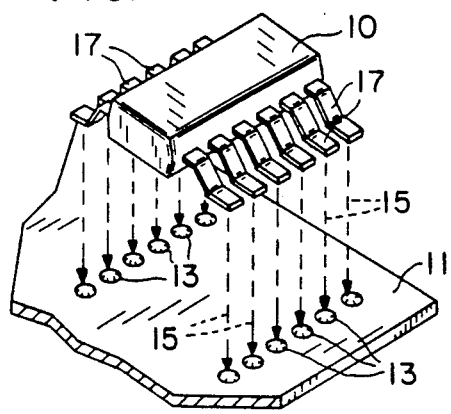
FIG. 1 is an exploded perspective view illustrating a gull wing surface mount device above a fragmentary portion of a PC board.

As shown in FIG. 1, a surface mounted device 10 is to be mounted on a PC board 11 by contacting with solder dots 13. The SMD 10 is lowered in the direction of arrows 15 until the leads 17 contact the solder dots 13 and connection is made.

Figure 2:
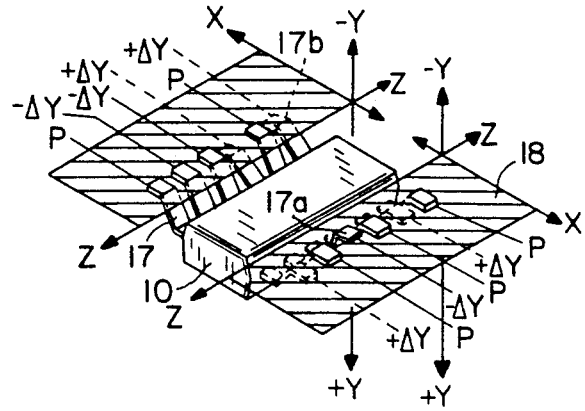
FIG. 2 is a perspective schematic view illustrating an SMD similar to that shown in FIG. 1, but shown in an inverted position and illustrating a non-coplanarity of the leads.

Shown in FIG. 2 is the SMD 10 of FIG. 1 with varying leads 17. These leads 17 are shown as gull wing leads, although other lead shapes such as "J" wing leads are equally applicable for the present invention. The particular style of lead and the particular electronics of the SMD are not part of the present invention, since this invention is operable for all designs.

In FIG. 2, some of the leads 17 are coplaner with the plane 18. In lowering the SMD 10 onto the printed circuit board 11, those leads 17 which are in coplanarity with plane 18 will mate suitably with the solder dots 13 and good connection will be achieved. However, some of the leads 17 are not in the plane 18 but extend out of plane by a distance, as shown by, for example, leads 17a, and 17b, along with the other leads in FIG. 2 as they deviate along the Y axis as shown. In the case of leads such as 17a, which extends further than the plane 18, there is a danger that the SMD 10 will be tilted and other leads will not make adequate contact with the solder dots 13. In the case of leads such as 17b, as shown in FIG. 2, the other leads being in contact with the PC board 11 may prevent the lead 17b from making contact. In either case, a defective assembly has been made.

In order to overcome the deficiencies of the prior art as shown in FIGS. 1 and 2, and to permit the location and correction of deviations in individual leads, the following apparatus has been developed in accordance with the principles of this invention. The SMD 10 is mounted on a linear motion mount 19 which is accurately moved by gear drive 21 back and forth as needed in the direction of double arrow 23. An accurate motor 25 is provided to precisely move the linear motion mount 19, in increments of very small dimensions or continuously at a slow rate of travel.

In the case of a dual sided SMD, such as the SMD 10 shown in FIGS. 1 and 2, the following arrangement is provided. Four-sided SMDs and SMDs with J wing leads and all of the many other designs are also completely within the scope of the present invention.

Figure 3:
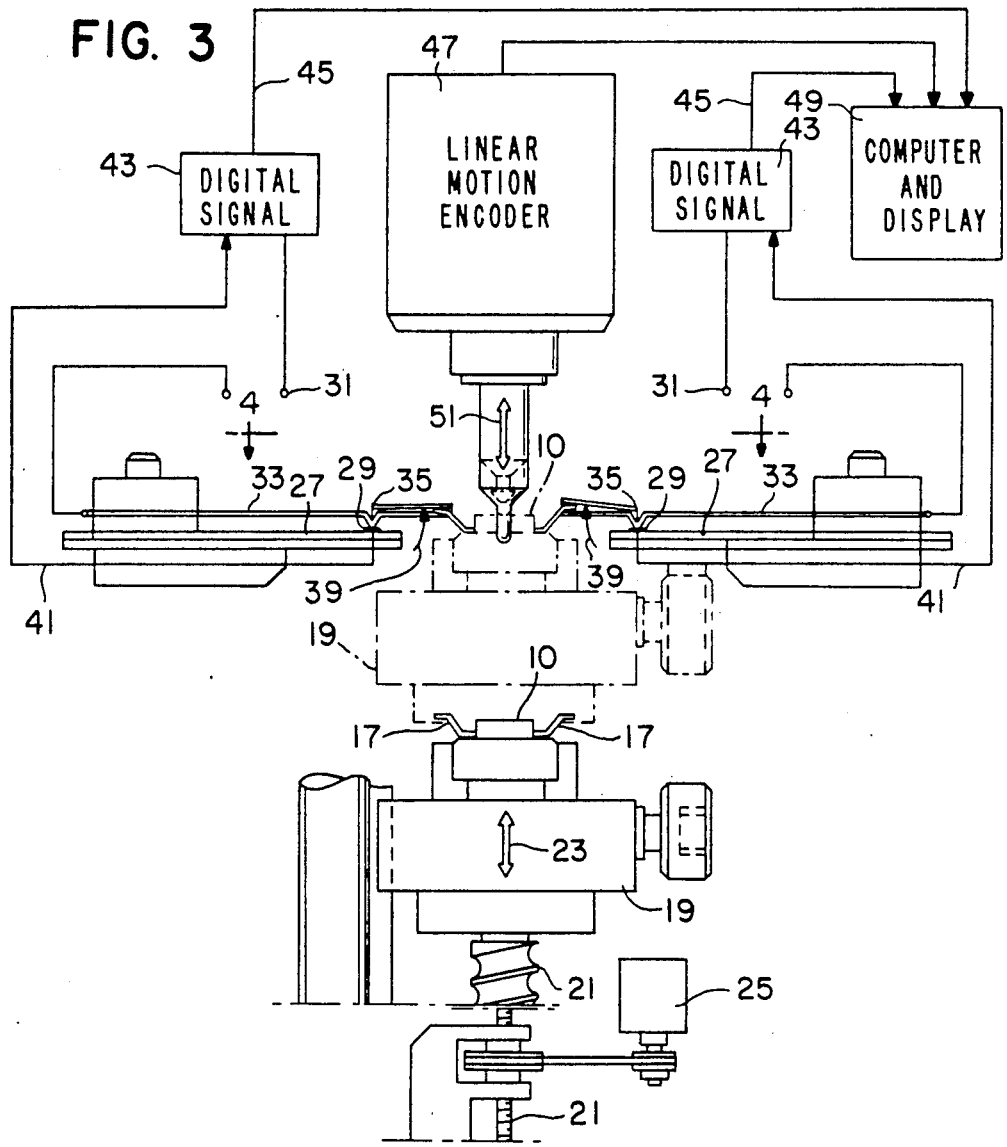
FIG. 3 is a semi-schematic elevational view showing a device for the testing of lead coplanarity of the SMD of FIGS. 1 and 2, all in accordance with the invention.

A switch is aligned in FIG. 3 to intersect with the leads 17 on both sides of the SMD 10. The switches includes a PC board 27 on which is deposited a conductive portion such as conductive gold run 29. The conductor 29 contact metallic tine 33 at contact point 35 to complete an electrical switch circuit when the tine 33 is in a predetermined position. The tine 33 is held in contact at contact point 35 by the built in bias in the stainless steel. Normally, before the system is in use, the tine 33 is biased to contact conductor 29 at 35 and is designed to move in the direction of arrow 39 when subjected to pressure from an object being moved along the axis of arrow 23. When contacted by an object moving the direction of arrow 23, a gap 37 is formed between conductor 29 and tine 33.

When the linear motion mount 19 brings the leads 17 of the SMD 10 into contact with the tines 33, and reaches the position shown by the linear motion mount, shown in dot-dash lines, gap 37 breaks the circuit, stopping curved flow in line 41. When this signal interruption stops current flow in line 41, digital converter 45 sends a signal to computer 49. At the same time, the linear motion encoder 47 measures the actual position of the linear motion mount 19 and also provides a signal. Computer 49 determine the location of the circuit interruption for each tine 33 and each lead 17. Computer 49 also determines the signal from reference points, to compare expected planarity with real data. Digital signal unit 47 is connected to ground at 31.

Figure 4:
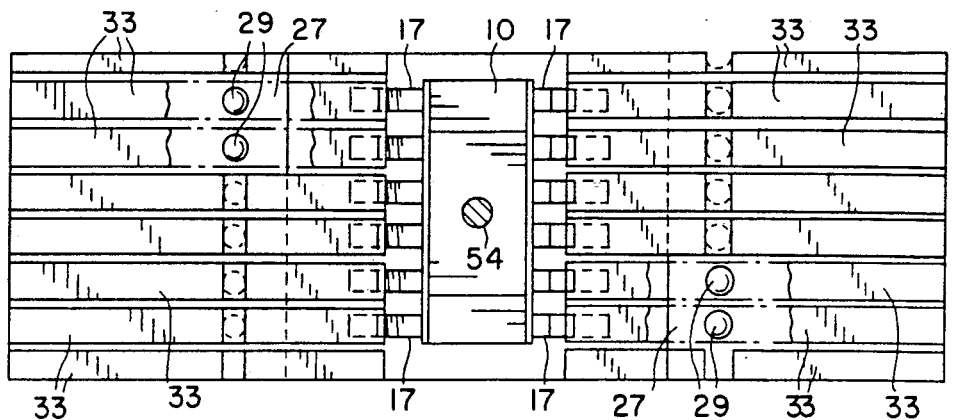
FIG. 4 is a slightly enlarged, fragmentary bottom plan view taken along lines 4—4 of FIG. 3, with some parts broken away to more clearly illustrate certain details of construction.

As shown in FIG. 4, in a slightly enlarged fragmentary bottom plane view taken along lines 4—4 of FIG. 3, with some parts missing, certain detail of the switch are shown. Specifically, gold conductors 29 are shown in alignment with the tines 33 and it is clear from this figure how the individual leads 17 of the SMD 10 contact individual tines 33. In this figure, the gull wing SMD 10 is shown with its associated lead pads 17 in contact with the outermost unsupported terminal ends of the tines 33 of the PC board 27.

Figure 5:
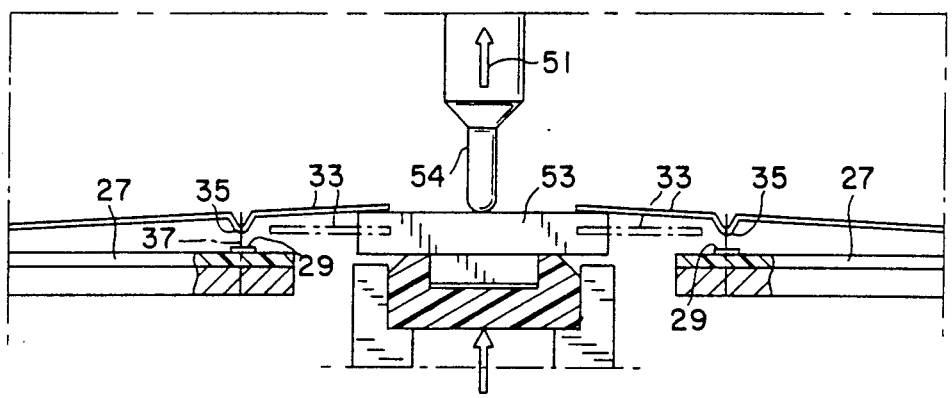
FIG. 5 is an enlarged fragmentary elevational view with portions broken away and in section to show additional detail of one embodiment of this invention, showing a reference gage being used.

In FIG. 5, the upper end of the linear motion mount 19 has been moved forward in the direction of arrow 51 until the gage block 53 has intersected the various tines 33. Initially, as was shown in FIG. 3, the tines 33 are resting on conductors 29 with contact points 35. As the plane of the gage block 53 engages tines 33, they are moved along the direction of the path, as shown by arrow 51, until a gap 37 is formed. At this time, the circuit is interrupted and a signal is generated. As each of the many tines 33 in the unit are deflected, reference points are placed in the computer memory. Since the gage block 53 is carefully machined to have a true plane surface, the point at which each tine 33 in the total device causes a signal to be generated by reaching the point of separation, shown by gap 37, for example, is recorded as a reference signal for that particular tine 33.

Stated another way, each of the individual tines 33 have been deflected by the coplaner surface of the gage block 53 by a distance so that all of the tines fall within the profile of the gage block. In one embodiment, a probe 54 contacts the center of the gage block 53 and records the location in incremental changes, such as every 0.0001 inches. This information is conveyed to the linear motion encoder 47 which generates a signal for each predetermined increment in elevational change of the gage block 53. That information is stored simultaneously with the signal generated as each tine 33 reaches the position on the path of arrow 23 that causes gap 37 to issue a signal change.

Figure 6:
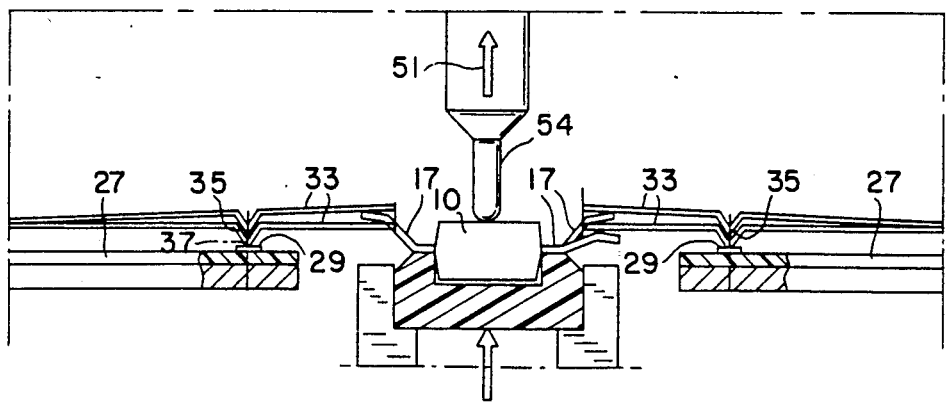
FIG. 6 is an enlarged fragmentary, elevational view similar to FIG. 5, showing a gull wing SMD being tested.

In FIG. 6, the same apparatus is employed, with a SMD device 10 being substituted for the gage block 53. Probe 54 is calibrated to read the same starting point that it did when gage block 53 began travel along the direction of arrow 51. Again, the increments are recorded by the linear motion encoder 47 and those signals are transmitted to the computer and display device 49. In this particular case, the SMD 10 includes, a plurality of leads 17. Initially, of course, all of the contact points 35 of the tines are resting on the conductor 29. As the SMD 10 travels in the direction of arrow 51, probe 54 notes the linear location. In FIG. 6, one lead 17 extends above the coplanarity which is desired. Therefore, that lead 17 intersects its tine 33 ahead of the rest of the tines. As tine 33 reaches the point when gap 37 is formed and contact 35 is separated from conductor 29, a signal is sent by the digital signal device 43, the computer 49. At each time when the signal is sent indicating the arrival of a certain tine at its signal sending location, the linear distance is also recorded. In the case where the lead 17 is not sufficiently coplaner as shown in FIG. 6, the tine 33 will not be deflected from contact point 35. Instead, the circuit will not activate detector 43 until a later time. Eventually, subject to limit switches which would prevent damage to the machine, each of the tines 33 will convey a signal as they are interacted by the leads 17.

It is now possible to determine which leads, if any, have deviated from coplanarity by an amount which has been predetermined to be problematic. Specifically, the computer calculates the difference between the actual linear location of the deflection for each lead and compares that location with the reference location which was generated when the gage block intersected the same tines. If the difference in location between the reference value and the actual value is 0, or is within a predetermine acceptable tolerance, coplanarity will have been achieved. If the difference between the signal from an individual tine which has been displaced by a particular lead is greater than the acceptable deviation from the reference signal corresponding to that time, the operator will be notified. In some instances, the SMD is merely rejected. In other more sophisticated systems, the SMD is withdrawn from the contact with the tines, the offending lead is adjusted either up or down depending upon the information which has been determined from the first measurement, and recheck is done. If the adjustment is proper, the lead will now be within the acceptable limits of coplanarity and the device can be passed as an acceptable device. It is within the scope of the individual assembly procedures to determine when and how deviated leads are corrected.

What is claimed is:

1. Apparatus for determining coplanarity of a plurality of points, comprising:
   linear motion means for moving an object along an linear axis, said object having a plane generally perpendicular to said axis;
   gage means defining a known plane also perpendicular to said axis and having a plurality of points thereon corresponding to points on said object, said gage means also being adapted to move along said axis by said linear motion means;
   digital signal means having individual sensors aligned on said axis for contact with said object and said gage to provide a set of signals to indicate the position of said object along said axis at each of said points and to provide a reference set of signals when contacted by said corresponding points on said gage plane; and comparator means for comparing said signals with said reference signals for each point and the corresponding point in said gage plane to identify the deviation of each point from coplanarity.

2. The apparatus of claim 1 wherein said digital signal means includes a plurality of flexible tines positioned along said axis for intersection with said object at a point along said axis, said signal means further including conductive leads for each tine positioned in normal circuit completing contact with each tine, each of said tines being movable upon contact with an object to a circuit breaking position out of contact with said conductive lead to thereby produce a digital signal indicating the contact between the tine and the object at a measured point along said axis.

3. The apparatus of claim. 2 wherein said object is a multiple lead device.

4. The apparatus of claim 2 wherein said object comprises a multiple lead device having a plurality of leads, each of which leads is aligned to contact one of said individual sensors.

5. The apparatus of claim 4 wherein said reference object is a gage means defining a know plane having points thereon corresponding to the location of said leads in said reference plane.

6. The apparatus of claim 2 wherein said tines are biased for contact with said conductive leads.

7. A digital signal device, comprising:
means for moving objects along a predetermined axis; and
signal generating circuit means for generating a signal including a plurality of flexible tines positioned along said axis for intersection with said object at a point along said axis, said circuit means further including conductive leads for each tine positioned in normal circuit completing contact with each tine, each of said tines being movable upon contact with an object to a circuit breaking position out of contact with said lead to thereby produce a digital signal indicating contact between said tine and said object at a point of said axis.

8. The device of claim 7 wherein said object is a multiple lead device.

9. The device of claim 7 wherein said object comprises a multiple lead device having a plurality of leads, each of which leads is aligned to contact one of said individual sensors.

10. The device of claim 7 wherein said reference object is a gage means defining a know plane having points thereon corresponding to the location of said leads in said reference plane.

11. The apparatus of claim 7 wherein said tines are biased for contact with said conductive leads.

* * * * *